United States Patent
Berkelman et al.

(10) Patent No.: US 9,766,213 B2
(45) Date of Patent: Sep. 19, 2017

(54) INNOVATION TO ASSAY MIXING

(71) Applicant: Bio-Rad Laboratories, Inc., Hercules, CA (US)

(72) Inventors: Tom R. Berkelman, Oakland, CA (US); Adriana Jeanne Harbers, Martinez, CA (US); Jovencio Hilario, Hercules, CA (US); Michael Keith Urban, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 264 days.

(21) Appl. No.: 14/505,227

(22) Filed: Oct. 2, 2014

(65) Prior Publication Data

US 2015/0090343 A1    Apr. 2, 2015

Related U.S. Application Data

(60) Provisional application No. 61/885,766, filed on Oct. 2, 2013.

(51) Int. Cl.
*G01N 21/59* (2006.01)
*G01N 21/31* (2006.01)
(Continued)

(52) U.S. Cl.
CPC ............. *G01N 30/04* (2013.01); *G01N 30/26* (2013.01); *G01N 30/8665* (2013.01); *Y10T 137/0324* (2015.04)

(58) Field of Classification Search
CPC .... G01N 21/59; G01N 21/31; G01N 30/8665; G01N 30/26; G01N 30/04; Y10T 137/0324
(Continued)

(56) References Cited

U.S. PATENT DOCUMENTS 4,805,623 A    2/1989  Jöbsis
6,241,788 B1 *  6/2001  Buentello ........... C09B 67/0073
                                                    8/607
(Continued)

FOREIGN PATENT DOCUMENTS

WO        00/45957 A1    8/2000

OTHER PUBLICATIONS

The International Search Report and Written Opinion from Appl. No. PCT/US2014/058893, mailed Feb. 10, 2015.
(Continued)

*Primary Examiner* — Daniel S Larkin
(74) *Attorney, Agent, or Firm* — Kilpatrick Townsend & Stockton LLP

(57) ABSTRACT

Methods, articles of manufacture, and kits for calibrating fluid delivery systems are provided. A fluid delivery system connected to N input streams, where N is an integer greater than or equal to 2, mixes together fluid from the N input streams to form an output stream. The methods involve obtaining N test solutions, each containing a dye, providing optical absorbances of the test solutions at appropriate wavelengths, injecting the test solutions into the input streams, mixing the test solutions, and measuring the absorbance of the output stream at the same wavelengths. The methods also involve comparing the absorbances of the test solutions with the absorbances of the output stream, which can include calculating ratios and comparing the ratios with target values. The methods can further involve adjusting operation of the fluid delivery system based upon the absorbances. In some embodiments, the dyes have largely non-overlapping absorbance spectra.

18 Claims, 6 Drawing Sheets

(51) Int. Cl.
G01N 30/04 (2006.01)
G01N 30/26 (2006.01)
G01N 30/86 (2006.01)

(58) Field of Classification Search
USPC .............. 73/1.01, 1.02, 1, 3; 356/433; 137/2
See application file for complete search history.

(56) References Cited

U.S. PATENT DOCUMENTS

| | | |
|---|---|---|
| 2002/0134143 A1 | 9/2002 | Allington et al. |
| 2004/0007675 A1 | 1/2004 | Gillispie et al. |
| 2007/0092407 A1 | 4/2007 | Xiao et al. |

OTHER PUBLICATIONS

Qi et al.; "Capillary electrophoresis of cardiolipin with on-line dye interaction and spectrophotometric detection"; *Electrophoresis*; 24:1680-1686 (2003).

Wheals et al.; "High-Performance Liquid Chromatographic Method Utilising Single or Multi-Wavelength Detection for the Comparison of Disperse Dyes Extracted From Polyester Fibres"; *J. Chromatog.*; 350:205-215 (1985).

Wood et al.; "Recent Applications of Liquid Chromatography-Mass Spectrometry in Forensic Science"; *J. Chromatoq. A*; 1130:3-15 (2006).

\* cited by examiner

MPTS

Pyrromethene 556

Sulforhodamine 101

Cardiogreen

INNOVATION TO ASSAY MIXING

CROSS-REFERENCES TO RELATED APPLICATIONS

This application claims the benefit of U.S. Provisional Application No. 61/885,766, entitled "INNOVATION TO ASSAY MIXING" and filed Oct. 2, 2013, the entire contents of which are incorporated herein by reference.

BACKGROUND OF THE INVENTION

Liquid chromatography is widely used to prepare and analyze biological samples, and to purify components of biological samples from contaminants. In liquid chromatography, a sample is suspended in a mobile phase, such as a buffer, which is passed over a stationary phase, such as a column. The binding of the sample, or particular components thereof, to the stationary phase, and the subsequent elution of the sample back into the mobile phase is controlled by altering the chemical environment to which the sample is exposed. This is typically done by changing the makeup of the mobile phase. Two or more buffers, containing disparate solute concentrations or having different pHs, for example, can be mixed together in gradually varying portions, and the resulting mixture can be applied to the column to cause binding and elution of the sample at the desired times. The parts of a liquid chromatography system that draw multiple buffers (or other liquids) from their source containers, mix the buffers together, and deliver the mixture to the column are together an example of a fluid delivery system.

In order to attain the desired level of control of sample binding and elution in liquid chromatography, the fluid delivery system must be properly calibrated. For example, the actual portion of each buffer in the mixture should be compared with the desired portion, across the full range of portions that might be encountered, and any disparities should be reduced or eliminated. If mixing can be turned off and the buffers can be kept separate while passing through the system, then the amounts of buffer that arrive at the column (or the rates at which they arrive) can be measured. However, this is not feasible in many fluid delivery systems, where buffer intake and mixing are tightly coupled. Alternatively, the rates at which the source containers decrease in mass can be measured, but this requires balances and other equipment that is typically not available in liquid chromatography setups.

The concentrations of biological species, such as proteins and nucleic acids, that pass through the column are often monitored using optical absorbance. Ultraviolet, visible, or infrared light is made incident upon the mobile phase as it exits the column, and the absorbance of the mobile phase is monitored at one or more wavelengths in real time. If the extinction coefficient of a species at a particular wavelength is known, then its concentration can be inferred. Absorbance measurements are not limited to biological species, can reflect components of the buffers that are mixed together in the fluid delivery system, and can be made upstream of (or in the absence of) the column.

BRIEF SUMMARY OF THE INVENTION

Provided herein are methods, articles of manufacture, and kits.

A method of calibrating a fluid delivery system is provided. The method involves providing a fluid delivery system connected to N input streams, where N is an integer greater than or equal to 2, and where the fluid delivery system mixes together fluids from the N input streams to form an output stream; and obtaining N test solutions, where each test solution includes a dye having a characteristic wavelength of maximum absorbance ($\lambda_{max}$). The method further includes, for each of the N test solutions, designating a wavelength $\lambda_{test}$, where $\lambda_{test}$ is about equal to $\lambda_{max}$, and providing an input absorbance of the test solution, the input absorbance being the absorbance of the solution at $\lambda_{test}$. The method also includes injecting the N test solutions into the N input streams; mixing the N test solutions in the fluid delivery system; measuring the absorbance of the output stream at N wavelengths, the wavelengths being the $\lambda_{test}$s designated for the test solutions, thereby obtaining an output absorbance for each test solution; and comparing the input absorbance with the output absorbance for each test solution, thereby calibrating the fluid delivery system.

In some embodiments of the method, N is 4.

In some embodiments of the method, $\lambda_{max}$ of the dye of any first test solution differs from $\lambda_{max}$ of the dye of any second test solution by at least about 50, 100, 200, or 300 nm. In other embodiments, the $\lambda_{test}$ designated for any first test solution differs from the $\lambda_{test}$ designated for any second test solution by at least about 50, 100, 200, or 300 nm. In still other embodiments, for each test solution, the $\lambda_{test}$ designated for the test solution and the $\lambda_{max}$ of the dye in the test solution differ by at most about 1, 5, 10, 20, or 50 nm.

In some embodiments of the method, the input absorbance of each test solution is in the range of about 0.1 to about 1.1. In one of these embodiments, the input absorbance of each test solution is about 0.1, 0.5, or 1.0. In other embodiments, the input absorbances of any two test solutions differ by at most about 0.1. In still other embodiments, the input absorbances of any two test solutions differ by at most about 5%.

In some embodiments of the method, the input absorbance of any first test solution is at least about 10 times greater than the absorbance of any second test solution at the $\lambda_{test}$ of the first test solution. In other embodiments, the absorbance of any first test solution at the $\lambda_{max}$ of the dye of the first test solution is at least about 10 times greater than the absorbance of any second test solution at the same $\lambda_{max}$. In yet other embodiments, the input absorbance of any particular test solution is at least about 10 times greater than the sum of the absorbances of the remaining test solutions at the $\lambda_{test}$ of the particular test solution. In still other embodiments, the absorbance of any particular test solution at the $\lambda_{max}$ of the dye of the particular test solution is at least about 10 times greater than the sum of the absorbances of the remaining test solutions at the same $\lambda_{max}$.

In some embodiments, the fluid delivery system is further connected to a multi-wavelength detector. In some embodiments, each output absorbance is measured spectrophotometrically.

In some embodiments of the method, the dyes of the test solutions are organic dyes such as pyrenes, boron-dipyrromethenes (BODIPYs), rhodamines, or indocyanines. In some embodiments, the dyes are sulfonated aromatic dyes. In one such embodiment, each dye includes at least two of the following functional groups: sulfonate ($-SO_3^-$) or sulfonic acid ($-SO_3H$). In another such embodiment, the dyes of the test solutions are pyrenes, boron-dipyrromethenes (BODIPYs), rhodamines, or indocyanines. In still another such embodiment, the dyes of the test solutions are MPTS, pyrromethene 556, sulforhodamine 101, and/or cardiogreen.

In some embodiments of the method, the fluid delivery system includes a pump. In some of these embodiments, the pump is a positive displacement pump. In one such embodiment, the pump is a piston pump.

In some embodiments of the method, the fluid delivery system includes at least N valves and at least one valve is associated with each input stream. In some embodiments, the fluid delivery system includes a multi-valve unit associated with at least two input streams. In one of these embodiments, the multi-valve unit is associated with all N input streams. In other embodiments, the fluid delivery system includes a valve associated with at least two input streams. In one such embodiment, the valve is associated with all N input streams.

In some embodiments, the fluid delivery system is further connected to a chromatography column. In one of these embodiments, the output stream is passed into the chromatography column.

In some embodiments, the method also includes adjusting the operation of the fluid delivery system based upon the input absorbance and the output absorbance of at least one test solution.

In some embodiments of the method, the comparing step includes, for each test solution, dividing the output absorbance by the input absorbance to obtain a ratio, which provides an estimate of the portion of the output stream comprising the test solution. In one such embodiment, the ratio for one test solution is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In another such embodiment, the ratio for one test solution is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In still another such embodiment, the ratios for the N test solutions are all at least about 0.001, 0.002, 0.005, 0.01, 0.02, 0.03, 0.04, 0.05, 0.1, 0.2, 0.3, 0.4, or 0.5. In yet another such embodiment, the ratios for the N test solutions are all at most about 0.1, 0.2, 0.3, 0.4, 0.5, 0.9, 0.95, 0.96, 0.97, 0.98, 0.99, 0.995, 0.998, or 0.999.

In some embodiments of the method that include obtaining a ratio for each test solution, the method also includes, for each test solution, designating a target portion for the test solution in the output stream, and comparing the ratio with the target portion; and the mixing occurs according to the target portions for the test solutions. In one such embodiment, the target portion for one test solution is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In another such embodiment, the target portion for one test solution is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In still another such embodiment, the target portions for the N test solutions are all at least about 0.001, 0.002, 0.005, 0.01, 0.02, 0.03, 0.04, 0.05, 0.1, 0.2, 0.3, 0.4, or 0.5. In yet another such embodiment, the target portions for the N test solutions are all at most about 0.1, 0.2, 0.3, 0.4, 0.5, 0.9, 0.95, 0.96, 0.97, 0.98, 0.99, 0.995, 0.998, or 0.999. In still another such embodiment, the difference between the ratio and the target portion for one test solution is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In yet another such embodiment, the difference between the ratio and the target portion for one test solution is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999.

In some embodiments of the method that include comparing ratios with target portions, the method also includes adjusting the operation of the fluid delivery system based upon the ratio and the target portion for at least one of the test solutions. In one embodiment, adjusting includes reducing the difference between the ratio and the target portion for at least one of the test solutions. In another such embodiment, the method further includes performing an additional calibration of the fluid delivery system after adjusting the operation of the fluid delivery system, such that the difference between the ratio and the target portion after adjusting operation of the fluid delivery system is smaller than the difference between the ratio and the target portion before adjusting operation of the fluid delivery system.

Also provided herein is a method of iteratively calibrating a fluid delivery system. The method includes: providing a fluid delivery system connected to N input streams, where N is an integer greater than or equal to 2, and where the fluid delivery system mixes together fluids from the N input streams to form an output stream; providing N test solutions; designating a first target portion for at least one test solution in the output stream; adjusting operation of the fluid delivery system based upon the first target portion; calibrating the fluid delivery system a first time, as described above; designating a second target portion for the at least one test solution in the output stream; adjusting operation of the fluid delivery system based upon the second target portion; calibrating the fluid delivery system a second time, as described above; and further adjusting operation of the fluid delivery system based upon the output absorbance of the at least one test solution obtained from calibrating the fluid delivery system the first time, and the output absorbance of the at least one test solution obtained from calibrating the fluid delivery the second time. In some embodiments of this iterative method, the first target portion and second target portion differ by at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In other embodiments, the first target portion is larger than the second target portion. In one such embodiment, the first target portion is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In still other embodiments of the iterative method, the first target portion is smaller than the second target portion. In one such embodiment, the first target portion is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999.

An additional method of iteratively calibrating a fluid delivery system is also provided. The method includes: providing a fluid delivery system connected to N input streams, where N is an integer greater than or equal to 2 and where the fluid delivery system mixes together fluids from the N input streams to form an output stream; providing N test solutions; designating a target portion for at least one test solution in the output stream; calibrating the fluid delivery system a first time according to claim 1; adjusting operation of the fluid delivery system based upon the input absorbance and the output absorbance of the at least one test solution, and the target portion of the at least one test solution in the output stream; calibrating the fluid delivery system a second time according to claim 1; and further adjusting operation of the fluid delivery system based upon the change in the output absorbance of the at least one test solution between calibrating the fluid delivery system the first time and calibrating the fluid delivery system the second time.

Further provided is a method of mixing together fluids. This method includes: providing a fluid delivery system connected to N input streams, where N is an integer greater than or equal to 2 and the fluid delivery system has been calibrated as described above; injecting N input solutions into the N input streams; and mixing the N input solutions in the fluid delivery system to form the output stream.

Articles of manufacture are also provided herein. One such article of manufacture includes a computer-readable medium having instructions stored thereon that, in response to execution by a computer system, cause the computer system to perform calibration of a fluid delivery system. The fluid delivery system is connected to N input streams, where N is an integer greater than or equal to 2, and where the fluid delivery system mixes together fluids from the N input streams under the control of the computer system to form an output stream. The instructions are to adjust the operation of the fluid delivery system based upon the absorbance of one of the input streams, measured at a designated wavelength, and the absorbance of the output stream measured at the same wavelength.

Another article of manufacture provided herein includes a computer-readable medium having instructions stored thereon that, in response to execution by a computer system, cause the computer system to perform calibration of a fluid delivery system. The fluid delivery system is connected to N input streams, where N is an integer greater than or equal to 2, and where the fluid delivery system mixes together fluids from the N input streams under the control of the computer system to form an output stream. The instructions are to compare the absorbance of one of the input streams, measured at a designated wavelength, with the absorbance of the output stream measured at the same wavelength. In some embodiments, comparing involves dividing the absorbance of the output stream by the absorbance of the input stream to obtain a ratio. In one such embodiment, the ratio is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In another such embodiment, the ratio is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999.

In some embodiments of this article of manufacture, where the instructions involve obtaining a ratio, instructions are also included to: read a target portion, which represents the portion of the input stream in the output stream, mix together the N input streams according to the target portion, and compare the ratio with the target portion. In one such embodiment, the target portion is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In another such embodiment, the target portion is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In yet another such embodiment, the difference between the ratio and the target portion is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In still another such embodiment, the difference between the ratio and the target portion is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. Yet other such embodiments also include instructions to adjust the operation of the fluid delivery system based upon the ratio and the target portion. In one of these embodiments, the instructions to adjust further include instructions to reduce the difference between the ratio and the target portion.

A kit for calibrating a fluid delivery system is also provided. The kit includes N test solutions. N is an integer greater than or equal to 2, each test solution includes a dye having a characteristic wavelength of maximum absorbance ($\lambda_{max}$), and $\lambda_{max}$ of the dye of any first test solution differs from $\lambda_{max}$ of the dye of any second test solution by at least about 50 nm. In some embodiments of the kit, N is 4. In other embodiments, $\lambda_{max}$ of the dye of any first test solution differs from $\lambda_{max}$ of the dye of any second test solution by at least about 100, 200, or 300 nm. In still other embodiments, the absorbance of each test solution, measured at the $\lambda_{max}$ of the dye of the test solution, is about 0.1, 0.5, or 1.0. In yet other embodiments, the absorbance of any first test solution, measured at the $\lambda_{max}$ of the dye of the first test solution, differs from the absorbance of any second test solution, measured at the $\lambda_{max}$ of the dye of the second test solution, by at most about 0.1. In still other embodiments, the absorbance of any first test solution, measured at the $\lambda_{max}$ of the dye of the first test solution, differs from the absorbance of any second test solution, measured at the $\lambda_{max}$ of the dye of the second test solution, by at most about 5%. In yet other embodiments, the absorbance of any first test solution at the $\lambda_{max}$ of the dye of the first test solution is at least about 10 times greater than the absorbance of any second test solution at the same $\lambda_{max}$. In still other embodiments, the absorbance of any first test solution at the $\lambda_{max}$ of the dye of the first test solution is at least about 10 times greater than the sum of the absorbances of the remaining test solutions at the same $\lambda_{max}$.

In some embodiments of the kit, the dyes of the test solutions are organic dyes such as pyrenes, boron-dipyrromethenes (BODIPYs), rhodamines, or indocyanines. In some embodiments, the dyes are sulfonated aromatic dyes. In one such embodiment, each dye includes at least two of the following functional groups: sulfonate ($-SO_3^-$) or sulfonic acid ($-SO_3H$). In another such embodiment, the dyes of the test solutions are pyrenes, boron-dipyrromethenes (BODIPYs), rhodamines, or indocyanines. In still another such embodiment, the dyes of the test solutions are MPTS, pyrromethene 556, sulforhodamine 101, and/or cardiogreen.

In some embodiments, the kit also includes a computer-readable medium having instructions stored thereon that, in response to execution by a computer system, cause the computer system to perform calibration of a fluid delivery system. The fluid delivery system includes N input streams, where the fluid delivery system mixes together fluid from the N input streams under the control of the computer system to form an output stream. The instructions are to adjust the operation of the fluid delivery system based upon the absorbance of one of the input streams, measured at a designated wavelength, and the absorbance of the output stream measured at the same wavelength.

In other embodiments, the kit also includes a computer-readable medium having instructions stored thereon that, in response to execution by a computer system, cause the computer system to perform calibration of a fluid delivery system. The fluid delivery system includes N input streams, where the fluid delivery system mixes together fluid from the N input streams under the control of the computer system to form an output stream. The instructions are to compare the absorbance of one of the input streams, measured at a designated wavelength, with the absorbance of the output stream measured at the same wavelength.

Figure 1:
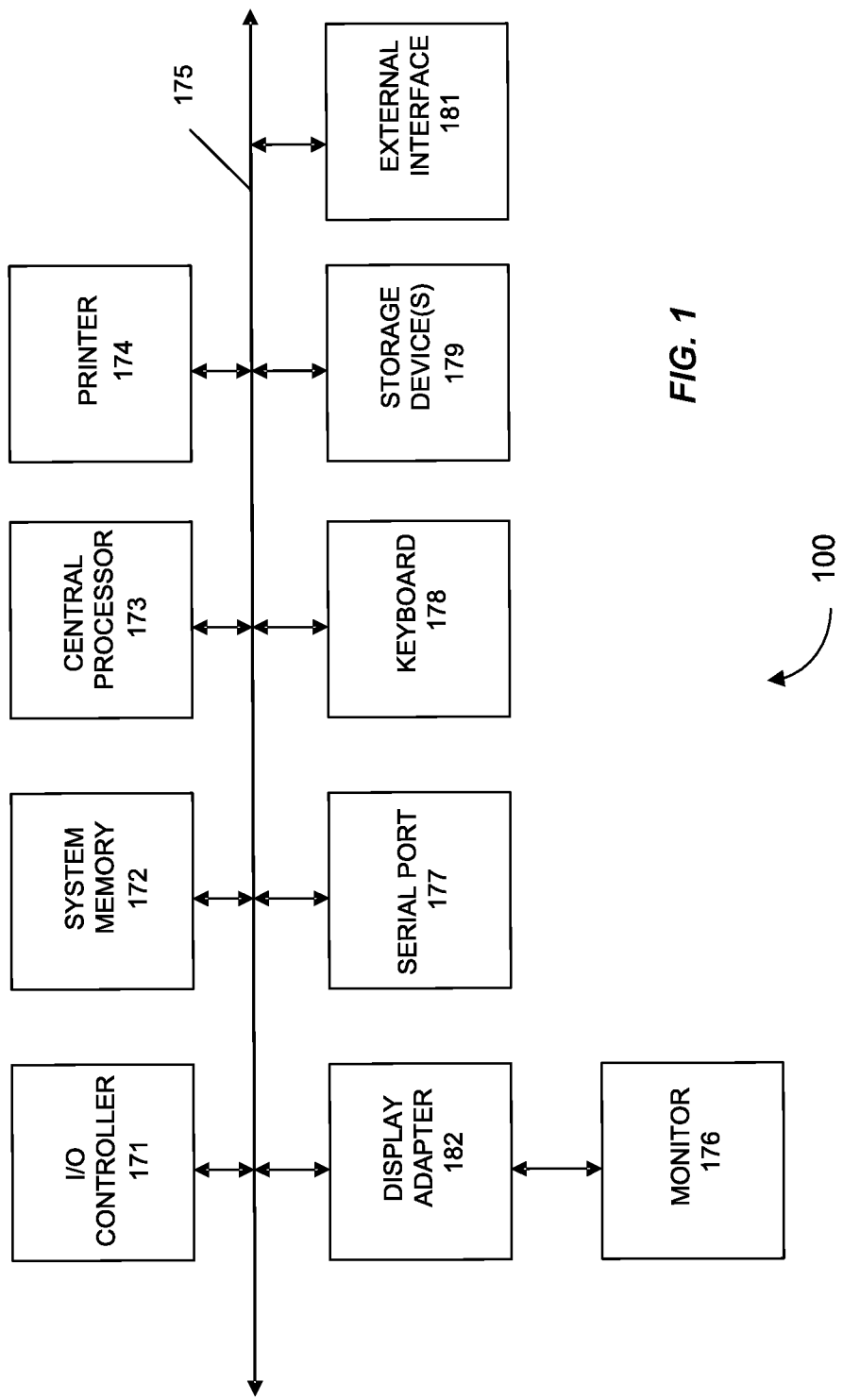
FIG. 1 shows a computer system for use with some embodiments of the invention.

Table 1 lists the dyes and $\lambda_{test}$ values of the test solutions used in Examples 2-4.

Table 2 lists the target portions for the test solutions used in Example 4.

DETAILED DESCRIPTION OF THE INVENTION

Introduction

The inventors have surprisingly discovered that fluid delivery systems can be calibrated using multiple dyes with largely non-overlapping absorbance spectra. A solution of each dye, called a test solution, can be prepared before calibration and the optical absorbance of the dye in the test solution, at or near the characteristic wavelength of maximum absorbance for the dye, can be measured or otherwise obtained. The test solutions can then be injected into the fluid delivery system and mixed together, resulting in a mixture that contains two or more dyes. The absorbance of this mixture can be measured at the same wavelengths used to obtain the absorbances of the test solutions. By comparing the absorbance of a particular test solution with the absorbance of the mixture measured at the same wavelength, the portion of test solution in the mixture can be determined. This information can then be used to calibrate the fluid delivery system, such as by adjusting its operation to bring the portion of the test solution in the mixture closer to a target value. In some embodiments, the fluid delivery system includes one or more valves, pumps, and/or mixing devices that operate in concert to determine the portion of each test solution in the mixture. Provided herein are methods, kits, and articles of manufacture for carrying out embodiments of the invention.

Definitions

The term "fluid delivery system" refers to a system that can deliver one or more fluids in a controlled manner to a downstream application. As used herein, "in a controlled manner" can mean that the amounts, rates of delivery, pressures, compositions, portions, or other characteristics of the fluids are within the control of the operator of the system and vary as desired by the operator. For example, a single fluid can be delivered in a controlled manner at a constant flow rate, at a constant level of pressure, at flow rates or pressures that fall within certain tolerances, or at flow rates or pressures that vary predictably or in programmed patterns over time. In the case of a fluid delivery system that handles two or more fluids, where the fluids are mixed or blended together in particular portions, "controlled manner" can also refer to the manner in which these portions are targeted or realized. For example, the portions can be set by the operator of the fluid delivery system, realized using mechanical elements of the fluid delivery system and software controlling these elements, and maintained within certain tolerances over time. Mechanical components of the fluid delivery system can include one or more valves, pumps, and/or mixing devices. A "downstream application" can be understood to be any process (e.g. liquid chromatography), or any apparatus involved in such a process (e.g. a liquid chromatography column), that requires one or more fluids, or a mixture thereof, as its input.

The term "input stream" refers to a fluid that is introduced into a fluid delivery system, a container or channel for such a fluid, and/or the path that such a fluid follows. For example, an input stream can be a buffer, a bottle containing the buffer, or a section of tubing, leading from the bottle to the rest of the system, through which the buffer flows. An input stream can also be a coil of tubing, as used in liquid chromatography, into which a fluid can be injected, such as with a syringe. The fluid can then be carried into the fluid delivery system by changing the fluid connectivity of the coil, so that the injected fluid is drawn out of the coil by means of pressure or another fluid pushing the injected fluid along. Any materials or apparatus known in the art can be used to assemble an input stream. In the methods and apparatus disclosed herein, input streams are said to be upstream of the fluid delivery system.

The term "output stream" refers to the fluid that emerges from a fluid delivery system, after the fluids from any input streams have been mixed together. The term can also refer to a container or channel for the fluid emerging from the system, or the path that the fluid follows. The output stream is said to be downstream of the fluid delivery system and can be fed into any downstream application, such as a chromatography column.

The term "metering" refers to any means for controlling the movement or mixing of fluids. For example, in fluid delivery systems discussed herein, metering can pertain to the rates at which fluids arrive from the different input streams, the sequence in which the fluids arrive, the passage of the fluids through the system, or the relative amounts of these fluids in the output stream.

The term "characteristic wavelength of maximum absorbance ($\lambda_{max}$)" refers to the wavelength at which the optical absorbance of a chemical such as a dye is maximized. $\lambda_{max}$ can often be determined using a standard spectrophotometer, by plotting the absorbance spectrum of the chemical (i.e., absorbance versus incident wavelength) and locating the peak or maximal value of the spectrum. If the spectrum has multiple peaks, then $\lambda_{max}$ corresponds to the highest peak. For some chemicals, including dyes used in detecting biological macromolecules, $\lambda_{max}$ is well known and can be obtained from the literature. The shape of the absorbance spectrum of a chemical, including the locations of any peaks, is sensitive to the environment around the chemical and may depend on the solvent in which the chemical is suspended, the pH, or other factors.

As used herein, the terms "difference", "differ", and grammatical equivalents thereof refer to the absolute value of the difference between two numbers. That is, the difference between A and B is the same as the difference between B and A.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

Methods

In some embodiments, the methods involve providing a fluid delivery system. The fluid delivery system can be connected to N input streams, where N is an integer greater than or equal to 2, and can mix together fluids from the input streams to form an output stream. In some embodiments, N is 4. The fluid delivery system and any downstream applications, as defined above, can be arranged and connected to each other as desired (e.g., in line) or according to common practices in the art. For example, the fluid delivery system can be upstream of or part of a liquid chromatography system; such systems are described, for example, in *Introduction to Modern Liquid Chromatography,* 3rd ed., New York: Wiley, 2010.

The fluid delivery system can be configured to handle aqueous or organic fluids, or mixtures thereof. Without limitation, fluids such as aqueous buffers, aqueous solutions, organic solvents, and solutions containing inorganic salts, biological macromolecules, or organic small molecules, can be mixed together using the system. However, the range of fluids can be limited by the hardware employed in the fluid delivery system—for example, some kinds of tubing can be dissolved by strong acids and cannot be used to pass low-pH aqueous solutions. Fluids can be introduced into the fluid delivery system through the input streams. Prior to calibration, if desired, the system can be 'primed' by introducing fluids that are similar in composition to the test solutions described below.

The methods can further include obtaining N test solutions, each of which contains a dye having a characteristic wavelength of maximum absorbance ($\lambda_{max}$). Any dyes can be used in the test solutions, but in preferred embodiments the dyes strongly absorb visible, ultraviolet, or near-infrared light and have $\lambda_{max}$ values in these parts of the electromagnetic spectrum. Exemplary classes of organic dyes with these characteristics include pyrenes, boron-dipyrromethenes (BODIPYs), borodiazaindacenes, xanthenes, rhodamines, indocyanines, and heptamethine cyanines. Each dye can be covalently linked to one or more chemical substituents (for example and without limitation, hydroxyl, carboxyl, carbonyl, formyl, sulfonic, sulfhydryl, amino, azido, alkyl, alkenyl, alkynyl, phenyl, or aromatic groups), which can influence characteristics of the dye such as its solubility, $\lambda_{max}$, electronic structure, and chemical reactivity. In some embodiments, the dyes are sulfonated aromatic dyes. In some embodiments, each dye has at least two sulfonate ($-SO_3^-$) or sulfonic acid ($-SO_3H$) groups. Such dyes include 8-methoxypyrene-1,3,6-trisulfonic acid, trisodium salt (MPTS), disodium-1,3,5,7,8-pentamethylpyrromethene-2,6-disulfonate-difluoroborate complex (pyrromethene 556), hydrogen 9-(2,4-disulphonatophenyl)-2,3,6,7,12,13,16,17-octahydro-1H,5H,11H,15H-xantheno[2,3,4-ij:5,6,7-i'j']diquinolizin-18-ium (sulforhodamine 101), and sodium 4-[2-[(1E,3E,5E,7Z)-7-[1,1-dimethyl-3-(4-sulfonatobutyl)benzo[e]indol-2-ylidene]hepta-1,3,5-trienyl]-1,1-dimethylbenzo[e]indol-3-ium-3-yl]butane-1-sulfonate (cardiogreen).

The following compounds are examples of pyrenes for use as dyes in some embodiments of the invention: 1,3,6-trichloropyrene, 1,3,6,8-tetrachloropyrene, 1-methylpyrene, 1-pyrenol, 1-pyrenamine, 1-pyrenecarbaldehyde, 1-bromopyrene, 1-pyrenylmethanol, 1-ethynylpyrene, 1,3,6,8-tetraisopropylpyrene, 1,3,6,8-tetrabromopyrene, 1-(chloromethyl)pyrene, 1-pyrenylmethanamine hydrochloride, 1-(1-pyrenyl)ethanone, 1-pyrenylboronic acid, 1-pyrenecarboxylic acid, 1-pyrenyl thiocyanate, 1-pyrenecarbaldehyde hydrazine, N,N-dimethyl(1-pyrenyl)methanamine hydrochloride, 1-pyrenesulfonic acid hydrate, N,N-diethyl-1-pyrenamine, 1-(bromomethyl)pyrene, 1-(diazomethyl)pyrene (PDAM), 1-[(E)-2-(1-naphthyl)ethenyl]pyrene, 4-(1-pyrenyl)-1-butanol, 1-[(E)-2-(2-naphthyl)ethenyl]pyrene, 1-pyrenylacetic acid, 1-nitropyrene, sodium 1-pyrenesulfonate, 1,8-dinitropyrene, 1,6-dinitropyrene, 8-nitro-1-pyrenamine, 1-pyrenediazonium tetrafluoroborate, N-(1-pyrenyl)acetamide (1-acetamidopyrene), 4-(1-pyrenyl)butanoic acid, tetrasodium 1,3,6,8-pyrenetetrasulfonate hydrate, 1,3,6-trinitropyrene, 1,3-dinitropyrene, 12-(1-pyrenyl)dodecanoic acid, 10-(1-pyrenyl)decanoic acid, 4-oxo-4-(1-pyrenyl)butanoic acid, 2-(1-pyrenyl)ethyl chloridocarbonate, S-(1-pyrenylmethyl) methanesulfonothioate, 2-bromo-1-(1-pyrenyl)ethanone, 2,2,2-trifluoro-1-(1-pyrenyl)ethanol, 1,3,6,8-tetraphenylpyrene, disodium 6,8-dihydroxy-1,3-pyrenedisulfonate, 2-{[8-(2-carboxybenzoyl)-1-pyrenyl]methyl}benzoic acid, trisodium 8-amino-1,3,6-pyrenetrisulfonate, methyl (2Z)-3-(1-pyrenyl)-2-butenoate, 1-(1-pyrenyl)ethyl chloroacetate, trisodium 8-hydroxy-1,3,6-pyrenetrisulfonate, 1-pyrenylmethyl 2-methylacrylate, 4-(1-pyrenyl)butanohydrazide, 8-Hydroxy-N,N,N',N',N",N"-hexamethylpyrene-1,3,6-trisulfonamide, trisodium 8-methoxy-1,3,6-pyrenetrisulfonate, 8-methoxypyrene-1,3,6-trisulfonic acid, trisodium salt (MPTS), N-hexadecyl-1-pyrenesulfonamide, trisodium 8-isothiocyanato-1,3,6-pyrenetrisulfonate, 8-Ethoxy-N,N,N',N',N",N"-hexamethylpyrene-1,3,6-trisulfonamide, trisodium 8-(tetradecyloxy)-1,3,6-pyrenetrisulfonate, trisodium 8-(butyryloxy)-1,3,6-pyrenetrisulfonate, trisodium 8-(octadecyloxy)-1,3,6-pyrenetrisulfonate, myo-Inositol 1-[4-(1-pyrene)butyl phosphate], S-[3-oxo-3-(1-pyrenylamino)propyl] methanesulfonothioate, trisodium 8-(octanoyloxy)-1,3,6-pyrenetrisulfonate, trisodium 8-(dodecanoyloxy)-1,3,6-pyrenetrisulfonate, S-(2-{[4-(1-pyrenyl)butanoyl]amino}ethyl) methanesulfonothioate, 2,4-dichloro-6-(1-pyrenyl)-1,3,5-triazine, 1-{[4-(1-pyrenyl)butanoyl]oxy}-2,5-pyrrolidinedione, 1-(1-pyrenyl)-1H-pyrrole-2,5-dione, 1-Palmitoyl-2-(pyrene-1-yl)decanoyl-sn-glycero-3-phosphocholine, (3alpha)-cholest-5-en-3-yl 6-(1-pyrenyl)hexanoate, and (1R)-2-[(hydroxy{2-[(1-pyrenylsulfonyl)

amino]ethoxy}phosphoryl)oxy]-1-{[(9E)-9-octadecenoyloxy]methyl}ethyl (9E)-9-octadecenoate.

The following compounds are examples of boron-dipyrromethenes for use as dyes in some embodiments of the invention: disodium-1,3,5,7,8-pentamethylpyrromethene-2,6-disulfonate-difluoroborate complex (pyrromethene 556), 2,6-Diethyl-4,4-difluoro-1,3,5,7-tetramethyl-8-[4-(2-propinyloxy)phenyl]-4-bora-3a,4a-diaza-s-indacene (Bodipy-X-Alkyne), and 8-[4-(2-Azidoethoxy)phenyl]-2,6-diethyl-4,4-difluoro-1,3,5,7-tetramethyl-3a,4a-diaza-4-bora-s-indacene (Bodipy-X-Azide).

The following compounds are examples of rhodamines for use as dyes in some embodiments of the invention: 6-amino-9-(2-carboxyphenyl)-3H-xanthen-3-iminium hydrogen sulfate (rhodamine sulfate), N-{6-(dimethylamino)-9-[2-(methoxycarbonyl)phenyl]-3H-xanthen-3-ylidene}-N-methylmethanaminium perchlorate (tetramethylrhodamine methyl ester perchlorate), N-[9-(2-carboxyphenyl)-6-(diethylamino)-3H-xanthen-3-ylidene]-N-ethylethanaminium chloride (Rhodamine B), N-[9-(2-carboxy-4-isothiocyanatophenyl)-6-(diethylamino)-3H-xanthen-3-ylidene]-N-ethylethanaminium chloride (rhodamine B isothiocyanate), sodium 4-[6-(diethylamino)-3-(diethyliminio)-3H-xanthen-9-yl]-1,3-benzenedisulfonate (sulforhodamine B sodium salt), N-(6-(diethylamino)-9-{2-[(octadecyloxy)carbonyl]phenyl}-3H-xanthen-3-ylidene)-N-ethylethanaminium perchlorate (rhodamine B octadecyl ester perchlorate), 2-[6-(diethylamino)-3-(diethyliminio)-3H-xanthen-9-yl]-5-sulfobenzenesulfonate (Sulforhodamine B, acid form), 5-(chlorosulfonyl)-2-[6-(diethylamino)-3-(diethyliminio)-3H-xanthen-9-yl]benzenesulfonate (sulforhodamine B acid chloride), sodium 2-{(3Z)-6-anilino-3-[(4-sulfonatophenyl)iminio]-3H-xanthen-9-yl}benzoate (Acid Violet 30), 2-[6-(diethylamino)-3-(diethyliminio)-3H-xanthen-9-yl]-5-{[(2-{[methyl(dioxido)sulfanyl]sulfanyl}ethyl)amino]sulfonyl}benzenesulfonate (sulforhodamine methanethiosulfonate), 9-(2,5-bis{[(2,5-dioxo-1-pyrrolidinyl)oxy]carbonyl}phenyl)-3,6-bis(dimethylamino)xanthenium chloride (5-carboxy-tetramethylrhodamine N-succinimidyl ester), N-{6-(diethylamino)-9-[2-({[(5E)-9-(diethylamino)-5H-benzo[a]phenoxazin-5-ylidene]amino}carbonyl)phenyl]-3H-xanthen-3-ylidene}-N-ethylethanaminium chloride (Rhodanile Blue), hydrogen 9-(2,4-disulphonatophenyl)-2,3,6,7,12,13,16,17-octahydro-1H,5H,11H,15H-xantheno[2,3,4-ij:5,6,7-i'j']diquinolizin-18-ium, (Sulforhodamine 101), 16-[4-(chlorosulfonyl)-2-sulfonatophenyl]-3-oxa-9$1^{5},23-diazaheptacyclo[17.7.1.1^{5,9}.0^{2,17}.0^{4,15}.0^{23,27}.0^{13,28}]octacosa-1,4,9(28),13,15,17,19(27)-heptaen-9-ylium (Sulforhodamine 101 acidchloride or Texas Red), 16-(2-carboxylatophenyl)-3-oxa-9$1^{5},23-diazaheptacyclo[17.7.1.1^{5,9}.0^{2,17}.0^{4,15}.0^{23,27}.0^{13,28}]octacosa-1,4,9(28),13,15,17,19(27)-heptaen-9-ylium (rhodamine 101 inner salt), and 2-[6-(diethylamino)-3-(diethyliminio)-3H-xanthen-9-yl]-5-{[(3-{3-[4-(1-methyl-1H-indol-3-yl)-2,5-dioxo-2,5-dihydro-1H-pyrrol-3-yl]-1H-indol-1-yl}propyl)amino]sulfonyl}benzenesulfonate (RIM-1).

The following compounds are examples of indocyanines for use as dyes in some embodiments of the invention: 1,3,3-trimethyl-2-[(1E,3E,5E,7Z)-7-(1,3,3-trimethyl-1,3-dihydro-2H-indol-2-ylidene)-1,3,5-heptatrienyl]-3H-indolium iodide (1,1',3,3,3',3'-Hexamethylindotricarbocyanine iodide), 2-((E)-2-{(3E)-2-chloro-3-[(2E)-2-(3,3-dimethyl-1-propyl-1,3-dihydro-2H-indol-2-ylidene)ethylidene]-1-cyclohexen-1-yl}ethenyl)-3,3-dimethyl-1-propyl-3H-indolium perchlorate (IR-780 perchlorate), 2-[(1E,3E)-3-(3,3-dimethyl-1-octadecyl-1,3-dihydro-2H-indol-2-ylidene)-1-propenyl]-3,3-dimethyl-1-octadecyl-3H-indolium perchlorate, sodium 4-((2E)-2-{(2E,4E,6E)-7-[1,1-dimethyl-3-(4-sulfonatobutyl)-1H-benzo[e]indolium-2-yl]-2,4,6-heptatrienylidene}-1,1-dimethyl-1H-benzo[e]indol-3-yl)-1-butanesulfonate (Cardiogreen), sodium 2-{(1E,3E)-3-[3-(3-carboxypropyl)-1-ethyl-3-methyl-5-sulfonato-1,3-dihydro-2H-indol-2-ylidene]-1-propenyl}-1-ethyl-3,3-dimethyl-3H-indolium-5-sulfonate (fluorescent orange 547), 1-{6-[(2,5-dioxo-1-pyrrolidinyl)oxy]-6-oxohexyl}-2-[(1E,3E,5Z)-5-(1-ethyl-3,3-dimethyl-1,3-dihydro-2H-indol-2-ylidene)-1,3-pentadienyl]-3,3-dimethyl-3H-indolium chloride (NIR-641 N-succinimidyl ester), sodium 2-[(1E,3E,5E)-5-(3-{4-[(2,5-dioxo-1-pyrrolidinyl)oxy]-4-oxobutyl}-1-ethyl-3-methyl-5-sulfonato-1,3-dihydro-2H-indol-2-ylidene)-1,3-pentadienyl]-1-ethyl-3,3-dimethyl-3H-indolium-5-sulfonate (Fluorescent red 647 reactive), and sodium 2-[(1E,3E)-3-(3-{4-[(2,5-dioxo-1-pyrrolidinyl)oxy]-4-oxobutyl}-1-ethyl-3-methyl-5-sulfonato-1,3-dihydro-2H-indol-2-ylidene)-1-propenyl]-1-ethyl-3,3-dimethyl-3H-indolium-5-sulfonate (Fluorescent orange 547 reactive).

The dyes from different test solutions preferably have absorbance spectra with little overlap—that is, the absorbance spectrum of one dye does not significantly overlap that of any other dye. Lack of overlap can be manifested by differences in $\lambda_{max}$ between dyes. In some embodiments, $\lambda_{max}$ of the dye of any first test solution differs from $\lambda_{max}$ of the dye of any second test solution by at least about 50, 100, 200, or 300 nm. In addition, the dyes are preferably non-interacting, as the term is understood in the art. For example, the dyes do not strongly interact with the walls of containers, including elements of the fluid delivery system, in which the test solutions are held or through which they are passed. When dyes from different test solutions are mixed together, they preferably do not bind to each other or chemically react with each other, and the absorbance spectrum of each dye does not change significantly due to the presence of the other dyes. Each test solution can be prepared as desired, for example by dissolving the dye in an appropriate solvent, or by diluting a stock solution of the dye.

A second wavelength, $\lambda_{test}$, is then designated for each test solution. $\lambda_{test}$ is preferably about equal to $\lambda_{max}$ of the dye in the test solution, so that the absorbance of the test solution measured at $\lambda_{test}$ (referred to as the input absorbance) approaches that at $\lambda_{max}$ and strongly correlates with the concentration of the dye in the test solution. A value of $\lambda_{test}$ can be chosen that differs from $\lambda_{max}$, however, for a variety of reasons. These reasons can include, for example, the ease of measuring absorbance at the chosen $\lambda_{test}$; the difficulty of measuring absorbance at $\lambda_{max}$; the difficulty of preparing the test solution so that $\lambda_{max}$ remains the same from one preparation to the next; uncertainty over the precise value of $\lambda_{max}$ in the test solution; or the sensitivity of $\lambda_{max}$ to solvent conditions. In some embodiments, for each test solution, the $\lambda_{test}$ designated for the test solution and the $\lambda_{max}$ of the dye in the test solution differ by at most about 1, 5, 10, 20, or 50 nm.

Preferably, $\lambda_{test}$ wavelengths are chosen where minimal overlap occurs between the absorbance spectra of the N different dyes. This ensures that, after the test solutions are mixed together, the absorbance of the output stream at a particular $\lambda_{test}$ reflects mainly absorbance by the dye originating from the corresponding test solution. Such $\lambda_{test}$ wavelengths can be chosen to reflect the spacing between the $\lambda_{max}$ for the dyes of the different test solutions. In some embodiments, the $\lambda_{test}$ designated for any first test solution differs from the $\lambda_{test}$ designated for any second test solution by at least about 50, 100, 200, or 300 nm.

The input absorbance for each test solution can be provided during calibration, for example by measuring the absorbance of the test solution at $\lambda_{test}$. The measurement can be made using standard equipment, such as a benchtop spectrophotometer or a spectrophotometer integrated into a liquid chromatography flowpath, and can occur at any time before mixing. For example, the absorbance can be measured at the time the test solution is prepared or as the test solution is drawn (e.g. injected) into one of the input streams connected to the fluid delivery system. Input absorbance can also be inferred, using Beer's law or a similar relationship, if the extinction coefficient at $\lambda_{test}$ and the concentration of the dye in the test solution are known. Finally, the input absorbance can be provided as an exogenous parameter, without requiring the practitioner to make a measurement or perform a calculation, if the test solution is prepared in advance of the calibration.

The input absorbance for each test solution is determined by the concentration and extinction coefficient of the dye, and is preferably within the linear range of the optical absorbance scale. Here, the absorbance is linearly proportional to the dye concentration. In some embodiments, the input absorbance of each test solution is in the range of about 0.1 to about 1.1. In other embodiments, the input absorbance of each test solution is about 0.1, 0.5, or 1.0. The practitioner may also find it advantageous to choose dye concentrations such that the input absorbances of the test solutions are all roughly equal. This allows simpler comparisons between the absorbances of the output stream at the chosen $\lambda_{test}$ values, in order to determine the portions of each test solution in the output stream. In some embodiments, the input absorbances of any two test solutions differ by at most about 0.1. In other embodiments, the input absorbances of any two test solutions differ by at most about 5%.

Once the input absorbance of any first test solution has been provided, the absorbance of a second test solution at the $\lambda_{test}$ of the first test solution can optionally be measured. This measurement gives a sense of how much overlap occurs between the absorbance spectra of the dyes in the first and second test solutions, and allows the practitioner to correct absorbance measurements made of the output stream for such overlap. In some embodiments, the input absorbance of any first test solution is at least about 10 times greater than the absorbance of any second test solution at the $\lambda_{test}$ of the first test solution. Overlap between absorbance spectra can also be evaluated by measuring absorbance of the test solutions at the $\lambda_{max}$ values of the dyes. In some embodiments, the absorbance of any first test solution at the $\lambda_{max}$ of the dye of the first test solution is at least about 10 times greater than the absorbance of any second test solution at the same $\lambda_{max}$. Preferably, in general, the absorbance of any test solution at the designated $\lambda_{test}$, or at the $\lambda_{max}$ of the dye in the test solution, is much larger than the absorbance of any other test solution measured at these wavelengths. By measuring the absorbance of each test solution at all N values of $\lambda_{test}$ or $\lambda_{max}$, and summing the absorbances, a more complete picture of spectral overlap can emerge. In some embodiments, the input absorbance of any particular test solution is at least about 10 times greater than the sum of the absorbances of the remaining test solutions at the $\lambda_{test}$ of the particular test solution. In other embodiments, the absorbance of any particular test solution at the $\lambda_{max}$ of the dye of the particular test solution is at least about 10 times greater than the sum of the absorbances of the remaining test solutions at the same $\lambda_{max}$.

The present methods also involve injecting the test solutions into the N input streams and mixing the test solutions using the fluid delivery system. The test solutions can be injected or otherwise introduced into the input streams as desired, for example using syringes, loading coils, pressure differentials, or gravity. Injection of the test solutions can occur at any rate and in any order, and each test solution can comprise the entirety of the input stream into which it is injected, or be blended with a carrier fluid. The test solutions can be drawn into or through the input streams by the action of one or more pumps, which can be part of the fluid delivery system. In some embodiments, a positive displacement pump such as a piston pump is used.

The movement of the test solutions through the fluid delivery system can be metered by valves or other mechanical elements. For example, the system can include at least N individual valves, where at least one valve is associated with each input stream. Alternatively, valves can be part of one or more multi-valve units that each meter test solutions from multiple input streams. A multi-valve unit can switch among the input streams to which it is connected, so that it admits fluid from at most one of these input streams at a time. In some embodiments, all N test solutions are metered by one multi-valve unit (e.g. an N-valve unit or an N-way unit). A single valve (sometimes called a multi-port valve) can also be connected to multiple input streams and be used to admit and meter fluid from these input streams. Such a single valve, like a multi-valve unit, can switch among multiple input streams and admit fluid from them in succession, or from one input stream to the exclusion of the others. If desired, a single valve can be connected to all N input streams. Other arrangements of valves are possible.

Mixing of the test solutions in the fluid delivery system can then be achieved as desired. In some embodiments, the system combines small volumes or 'plugs' of fluid admitted from the input streams one at a time. Mixing of two or more fluids can be induced with turbulence, such as by passing the fluids near a rotating element such as a stir bar, or using the action of a pump. Alternatively, mixing can be accomplished passively, by passing by fluids over fixed obstacles within the system that disrupt smooth fluid flow. Other mechanisms of mixing, such as diffusion or convection, can also be employed. Together, mechanical elements of the fluid delivery system mix the test solutions and determine the portion of each test solution in the output stream. Any fluid delivery system falling within the scope of the definition above can be used. In preferred embodiments, the system produces an output stream that is homogeneous, i.e. of uniform composition.

As the test solutions are mixed, the absorbance of the output stream is measured at the N wavelengths designated for the test solutions (i.e., the $\lambda_{test}$). The absorbance measured at each $\lambda_{test}$ is considered an output absorbance for the test solution for which that $\lambda_{test}$ was designated, and can be compared with the corresponding input absorbance. This comparison allows calibration of the fluid delivery system. In some embodiments, the fluid delivery system includes or is connected to a multi-wavelength detector for measuring the output absorbances. In some embodiments, each output absorbance is measured spectrophotometrically. When the absorbance of the output stream is measured at multiple wavelengths, detector cross-talk can occur and correction of the measured absorbances may be desirable.

During calibration of the fluid delivery system, output absorbances can be measured continuously and at any time the output stream is flowing—for example, before injecting the test solutions, before mixing has commenced, while injection or mixing is ongoing, or after mixing has been completed. After injecting the test solutions, passage of a certain amount of time may be required for the output absorbances to equilibrate (i.e. stabilize) and reflect the metering and mixing of the test solutions. This amount of time is referred to as the "equilibration time", and can depend on factors such as the individual flow rates of the input streams, the overall flow rate of the output stream, or the portions of each test solution in the output stream. In preferred embodiments, an output absorbance used for comparison to an input absorbance is not acquired until after the equilibration time has elapsed. Equilibration can also be considered in terms of the volume of fluid that passes through the fluid delivery system. The "equilibration volume" is the amount of fluid that must pass into the output stream before the output absorbances equilibrate, or equivalently the amount that passes into the output stream during the equilibration time. Equilibration may be necessary upon introducing new test solutions or carrier fluids to the fluid delivery system, or after adjusting operation of the system, as described below.

The fluid delivery system can be connected to a chromatography column through which the output stream is passed. Such a setup is useful when the practitioner wishes to blend buffers in changing portions over time, and elute analytes from the column using concentration gradients. Buffer blending is commonly used in the chromatographic analysis and preparation of biological molecules such as proteins. The column can also be used during calibration to separate the dyes after they have exited the fluid delivery system. The dyes thus become separated spatially as well as spectrally, allowing their absorbances to be more easily measured.

Generally, calibration of the fluid delivery system can involve adjusting aspects of its operation before or after comparing the input and output absorbances. Adjusting operation of the system can include, for example, changing the mechanics of drawing fluids from one or more input streams, tuning the operation of mechanical elements (e.g. valves, pumps) that meter fluids, or altering how the system combines fluids. These adjustments can be made to parts of the system that handle the at least one test solution for which input absorbance and output absorbance were measured, or can be made to other parts of the system. The adjustments can be performed as desired, and the details will depend on the particular set-up of the fluid delivery system.

In some embodiments, comparing the input absorbance with the output absorbance for each test solution involves dividing the output absorbance by the input absorbance to obtain a ratio. This ratio provides an estimate of the portion of the output stream comprising the test solution. Because the test solutions together make up at most 100% of the output stream, the ratio for each test solution should fall between 0 and 1. Depending on factors such as the value of N, the hardware within the fluid delivery system used to meter and mix the test solutions, and parameters of operation of the system controlled by the practitioner, the ratio for each test solution typically exceeds a minimum or does not exceed a maximum. In some embodiments, the ratio for one test solution is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In some embodiments, the ratio for one test solution is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. Operation of the system can also be adjusted so that all test solutions occur in the output stream in portions (ratios) above a minimum or below a maximum. In some embodiments, the ratios for the N test solutions are all at least about 0.001, 0.002, 0.005, 0.01, 0.02, 0.03, 0.04, 0.05, 0.1, 0.2, 0.3, 0.4, or 0.5. In some embodiments, the ratios for the N test solutions are all at most about 0.1, 0.2, 0.3, 0.4, 0.5, 0.9, 0.95, 0.96, 0.97, 0.98, 0.99, 0.995, 0.998, or 0.999.

The methods provided herein can also include, for each test solution, designating a target portion for the test solution in the output stream. Mixing can then occur according to the target portions, and the ratio measured for each test solution after mixing can be compared with the corresponding target portion. Mixing can be carried out according to the target portions by, for example, controlling the rates or sequences in which the test solutions are introduced to the system, so that the volumes of the test solutions that are mixed are proportional to the target portions. In principle, any target portion can be set for each test solution, provided that the target portions (as well as the portions of any other fluids in the output stream) sum to about 1, and the target portion can be attained with the hardware in the fluid delivery system. In some embodiments, the target portion for one test solution is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In some embodiments, the target portion for one test solution is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. Target portions can also be designated so that the target portions for all test solutions exceed a minimum value or do not exceed a maximum value. In some embodiments, the target portions for the N test solutions are all at least about 0.001, 0.002, 0.005, 0.01, 0.02, 0.03, 0.04, 0.05, 0.1, 0.2, 0.3, 0.4, or 0.5. In some embodiments, the target portions for the N test solutions are all at most about 0.1, 0.2, 0.3, 0.4, 0.5, 0.9, 0.95, 0.96, 0.97, 0.98, 0.99, 0.995, 0.998, or 0.999. The operation of the fluid delivery system can be adjusted based upon the designated target portion and the measured ratio of output absorbance to input absorbance for at least one test solution.

The difference between the ratio measured for a test solution, as described above, and the target portion designated for the test solution can be calculated and used in calibration of the fluid delivery system. This difference gives a sense of how closely mixing is occurring according to the target portion. In some embodiments, the difference between the ratio and the target portion for one test solution is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In some embodiments, the difference between the ratio and the target portion for one test solution is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. A small difference suggests that processes such as injection of the test solution into one of the input streams, metering of the test solution in the fluid delivery system, and mixing of the test solution with other test solutions (and any other fluids), are well controlled, and generally that the system is well calibrated. By contrast, a large difference indicates that one or more of these processes may require adjustment, in some cases in concert with the corresponding processes for the other test solutions. The difference between the measured ratio and target portion can be compared with a threshold value to evaluate whether to make such adjustments, in which case the threshold value can be set by the practitioner as desired. In some embodiments, adjusting operation of the fluid delivery system can involve or result in reducing this difference for at least one test solution. The difference can also be used for characterizing the accuracy of mixing when the fluid delivery system is used in the absence of test solutions, with a downstream application.

The calibration methods described herein can be performed repeatedly or iteratively to improve agreement between the ratio of output absorbance to input absorbance for a test solution on the one hand, and the target portion designated for that test solution in the output stream on the other hand. For example, calibration of a fluid delivery system can be performed twice, with at least one test solution having the same target portion and mixing occurring according to this target portion in both calibrations. In some embodiments, the first calibration includes adjusting operation of the system after measuring the ratio of the test solution in the output stream, with the result that the difference between the ratio and test solution falls from the first calibration to the second.

Iterative calibration can also be performed without tracking this difference, but rather by monitoring changes in the output absorbance of at least one test solution from one calibration to the next. In one embodiment of such an iterative calibration procedure, a target portion is designated for the test solution and calibration is performed a first time, including measuring an output absorbance for the test solution. The operation of the fluid delivery system is then adjusted based upon the input and output absorbances of the test solution and the target portion. Calibration is performed a second time, and further adjustments made to the operation of the system are based on the change in the output absorbance. Thus, while adjustments after the first calibration are made in view of the target portion, adjustments made after subsequent calibrations mainly take into account the effects of previous adjustments on output absorbance. This procedure can cause the output absorbance to change as desired: for example, to move in one direction, stay constant, or converge upon a target value. The procedure does not require calculation of the output-to-input ratio, or the difference between this ratio and the target portion, after every calibration. The procedure can be useful when adjusting metering of other input streams, or testing the effects of different kinds of adjustments on output absorbance.

In other embodiments, when calibration is performed twice, different target portions can be designated for at least one test solution in each calibration. Here, before the first calibration, a first target portion is designated for at least one test solution, and the operation of the fluid delivery system is adjusted based on this first target portion. Similarly, before the second calibration, a second target portion is designated for the at least one test solution, and the operation of the system is adjusted based on the second target portion. In each calibration, the output absorbance of the test solution is measured as usual. The operation of the system can then be further adjusted based on these output absorbances.

Calibrating the system with different target portions lets the practitioner test whether disparate amounts of fluid can be metered from a particular input stream and incorporated into the output stream, with the desired levels of control and accuracy. A large difference between the first and second target portions can be useful for testing the dynamic range of the metering mechanism. In some embodiments, the first target portion and second target portion differ by at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. By contrast, a small difference between the first and second target portions can be used to test sensitivity, i.e. whether a small change in the target portion can be realized and the resulting change in output absorbance can be detected. Regardless of the magnitude of the difference between the first and second target portions, any target portions can be used in these methods. In some embodiments, the first target portion is larger than the second target portion. Here, the first target portion can be at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999, for example. In other embodiments, the first target portion is smaller than the second target portion. Here, the first target portion can be at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999, for example. Changing the target portion for one test solution may necessitate changing the target portions for other test solutions. In some cases, operation of the system can be adjusted based on the target portions designated and output absorbances measured for multiple test solutions.

Once a fluid delivery system has been calibrated, once or multiple times, according to the provided methods, it can be used to mix together fluids in well-controlled proportions. Such mixing can be performed in essentially the same way test solutions were mixed when calibrating the system. The fluids, termed 'input solutions', are injected into the input streams and mixed to form the output stream. There can be as many input solutions as input streams, i.e. N, and one input solution can be injected per input stream. The input solutions can comprise any fluids that the system is configured to handle, as discussed above, and need not include dyes. However, any optically absorbent species in the input solutions can be detected before and after mixing as desired, to verify the proportions of mixing or for other purposes.

Articles of Manufacture

Articles of manufacture provided herein comprise a computer-readable medium having instructions stored thereon that, in response to execution by a computer system, cause the computer system to perform calibration of a fluid delivery system. The computer-readable medium can be, for example, a memory-containing device, a hard-disk or other local storage space, or a network or cloud storage space, as such are known in the art and readily available. The instructions can be written in any computer language, for example Java, C++, or Perl. Further disclosure about computer-readable media, computer-executable instructions, and computer systems is provided below.

Fluid delivery systems that can be calibrated using the provided articles of manufacture are similar or identical to the fluid delivery systems described above. In some embodiments, a fluid delivery system is connected to N input streams, wherein N is an integer greater than or equal to 2, and mixes together fluid from the N input streams under the control of the computer system to form an output stream. Any or all components of the fluid delivery system, including valves, pumps, or stirring elements, can be controlled by the computer system using methods known in the art.

In some embodiments, the instructions stored on the computer-readable medium include instructions to adjust the operation of the fluid delivery system based upon the absorbance of one of the input streams, measured at a designated wavelength, and the absorbance of the output stream measured at the same wavelength. Adjusting operation of the system can be directed to valves, pumps, or other mechanical elements of the system and can affect the metering of one or more input streams into or through the system, including the input stream for which the absorbance is measured. For example, the rate at which fluid from the input stream is drawn into the system can be increased or decreased. Any optical absorbance of one of the input streams or the output stream can arise from a dye or other analyte dissolved or suspended therein. Any wavelength can be used to measure absorbance, and if a dye is present, this wavelength can correspond to $\lambda_{max}$ or $\lambda_{test}$, as defined above.

In some embodiments, the instructions stored on the computer-readable medium include instructions to compare the absorbance of one of the input streams, measured at a designated wavelength, with the absorbance of the output stream measured at the same wavelength. The comparison is preferably quantitative and involves manipulating the two absorbance values with a mathematical function. The result of the manipulation can be immediately presented to the practitioner or can be stored in memory for later use. In some embodiments, the instructions to compare include instructions to divide the absorbance of the output stream by the absorbance of the input stream to obtain a ratio. This ratio provides an estimate of the portion of the input stream for which the absorbance was measured in the output stream after mixing. In some embodiments, the ratio is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In some embodiments, the ratio is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. Attributes of the hardware used to meter and mix fluids place practical limitations on how closely this ratio can approach 0 or 1.

In addition to providing for calculating a ratio, the instructions can also include instructions to read a target portion, which represents the portion of the input stream in the output stream. The target portion, also discussed above in conjunction with methods of calibrating the fluid delivery system, can be stored in memory. The instructions can prompt the practitioner to input the target portion when calibrating the system, or can use a default value for the target portion, thereby requiring no input from the practitioner. A value input by the practitioner can also be stored for later use as the default value. Alternatively, the target portion can be calculated based on other inputs from the practitioner, the value of N, or other considerations. In some embodiments, the target portion is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In some embodiments, the target portion is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999.

Upon reading the target portion, the instructions then cause the N input streams to be mixed together according to the target portion, and compare the ratio with the target portion. Mixing according to the target portion results from the fluid delivery system being under the control of the computer system, and can be accomplished by metering the input solutions as discussed above. The comparison between the ratio and the target portion can include calculating their difference, as defined herein. In some embodiments, the difference between the ratio and the target portion is at most about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. In some embodiments, the difference between the ratio and the target portion is at least about 0.001, 0.002, 0.005, 0.01, 0.02, 0.03, 0.04, 0.05, 0.1, 0.2, 0.3, 0.4, 0.5, 0.9, 0.95, 0.96, 0.97, 0.98, 0.99, 0.995, 0.998, or 0.999. As discussed above, smaller differences indicate better calibration.

The instructions can further include instructions to adjust the operation of the fluid delivery system, as discussed above, based upon the ratio and the target portion. In some embodiments, the instructions reduce the difference between the ratio and the target portion.

Kits

Kits for use in calibrating fluid delivery systems are also provided. In some embodiments, such kits include test solutions as described above. For example, a kit can include N test solutions, where N is an integer greater than or equal to 2. Each test solution can include a dye having a characteristic wavelength of maximum absorbance ($\lambda_{max}$), and $\lambda_{max}$ of the dye of any first test solution can differ from $\lambda_{max}$ of the dye of any second test solution by at least about 50 nm.

In the provided kits, each test solution can have any of the characteristics described above, including the identity and concentration of the dye, the composition of the solution in which the dye is suspended, the $\lambda_{max}$ of the dye in the solution, and the absorbance of the solution at $\lambda_{max}$. The test solutions together can also have the same characteristics as those described above, in terms of the value of N, the relationships between the $\lambda_{max}$ values for the different dyes, and the absorbances of these dyes at various wavelengths. These kits can be used in the methods provided herein, and so the same considerations discussed above can apply when selecting dyes and designing test solutions. Preferably, the dyes chosen for the different test solutions have absorbance spectra that overlap each other minimally, and the solutions are prepared to absorb at comparable levels at the respective $\lambda_{max}$ values.

In addition to test solutions, the provided kits can include articles of manufacture as described above, for example a computer-readable medium having instructions stored thereon that, in response to execution by a computer system, cause the computer system to perform calibration of a fluid delivery system. The fluid delivery system can be connected to N input streams and mix together fluid from the N input streams under the control of the computer system to form an output stream. In some embodiments, the instructions comprise instructions to adjust the operation of the fluid delivery system based upon the absorbance of one of the input streams, measured at a designated wavelength, and the absorbance of the output stream measured at the same wavelength. In some embodiments, the instructions comprise instructions to compare the absorbance of one of the input streams, measured at a designated wavelength, with the absorbance of the output stream measured at the same wavelength.

Computer Systems

Any of the computer systems mentioned herein may utilize any suitable number of subsystems. Examples of such subsystems are shown in FIG. 1 in computer apparatus 100. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 1 are interconnected via a system bus 175. Additional subsystems such as a printer 174, keyboard 178, storage device(s) 179, monitor 176, which is coupled to display adapter 182, and others are shown. Peripherals and input/output (I/O) devices, which couple to I/O controller 171, can be connected to the computer system by any number of means known in the art, such as serial port 177. For example, serial port 177 or external interface 181 (e.g. Ethernet, Wi-Fi, etc.) can be used to connect computer system 100 to a wide area network such as the Internet, a mouse input device, or a scanner. The interconnection via system bus 175 allows the central processor 173 to communicate with each subsystem and to control the execution of instructions from system memory 172 or the storage device(s) 179 (e.g., a fixed disk, such as a hard drive or optical disk), as well as the exchange of information between subsystems. The system memory 172 and/or the storage device(s) 179 may embody a computer readable medium. Any of the data mentioned herein can be output from one component to another component and can be output to the user.

A computer system can include a plurality of the same components or subsystems, e.g., connected together by external interface 181 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that some of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission. Suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

The methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

EXAMPLES

Example 1

Figure 2A:
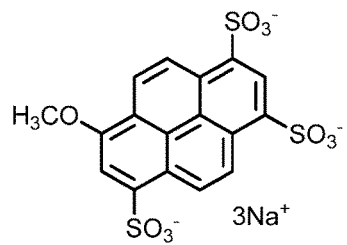
FIG. 2A shows structures of four polysulfonated aromatic dyes.
Figure 2A:
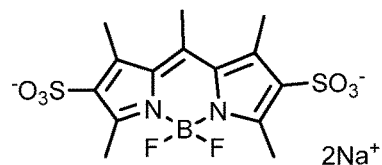
Figure 2A:
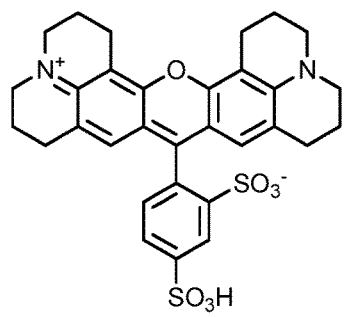
Figure 2A:
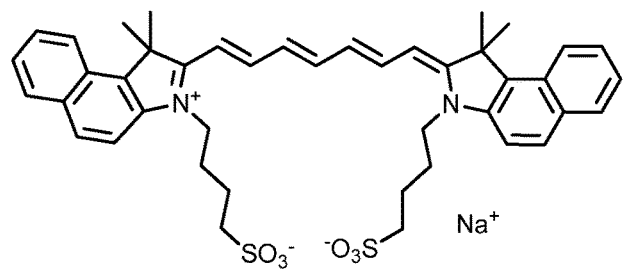
Figure 2B:
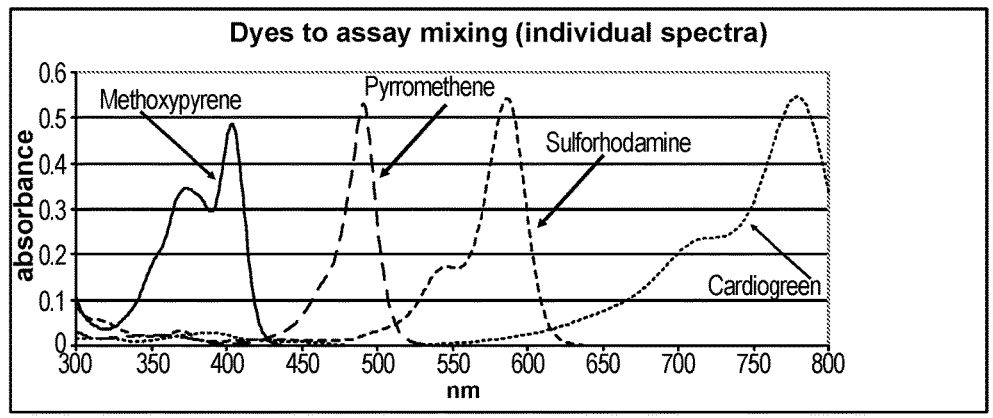
FIGS. 2B-D show absorbance spectra of these dyes. As described in Example 1, solutions of the individual dyes were prepared and optical absorbance spectra of these solutions were acquired (overlaid in FIG. 2B). These spectra were summed (FIG. 2C) and compared with a spectrum of a solution containing all four dyes (FIG. 2D).

Four dyes (MPTS, pyrromethene 556, sulforhodamine 101, and cardiogreen, structures shown in FIG. 2A) were evaluated for cross-interactivity and spectral overlap. Each dye was prepared as a 1% w/v solution in DMSO. Each solution was then diluted with water to such an extent that the absorbance of the solution at the $\lambda_{max}$ of the dye was roughly 0.5. Absorbance spectra of the four solutions from 300 to 800 nm were acquired and overlaid (FIG. 2B). At wavelengths near the peak of each spectrum, little absorbance was registered in the other three spectra, indicating a lack of spectral overlap between the four dyes.

Figure 2C:
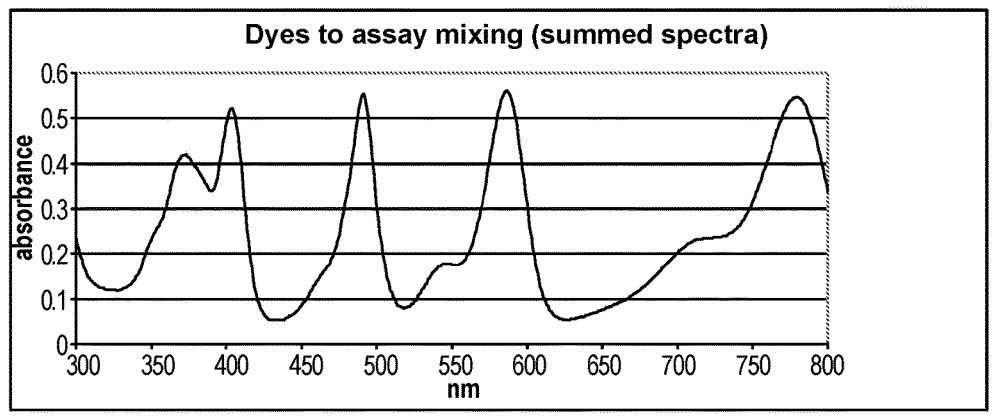
Figure 2D:
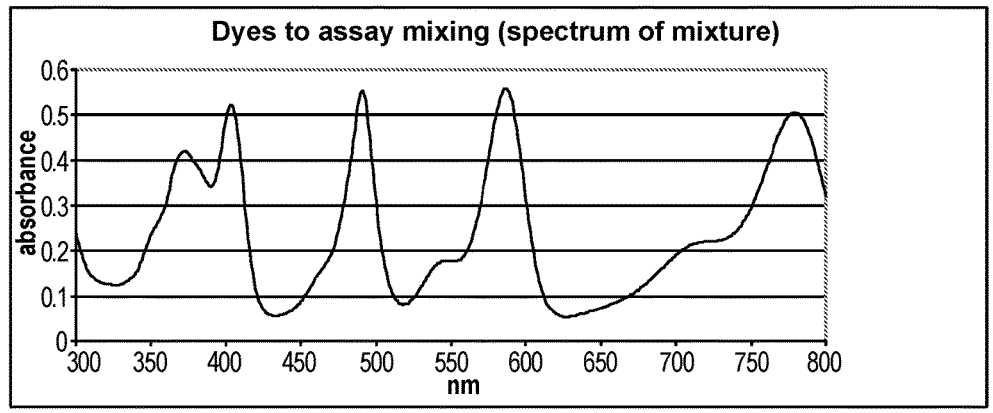

A mixture of the four dyes was then prepared in which the concentration of each dye was roughly equal to its concentration in the solution containing no other dyes. The sum of the individual spectra (FIG. 2C) appeared nearly identical to the spectrum of the mixture (FIG. 2D), indicating minimal interaction between the dyes when mixed together.

Example 2

Four test solutions were prepared, each containing one dye. The dyes and respective $\lambda_{test}$ values are provided in Table 1. Each test solution was prepared such that the input absorbance of the dye was 0.4 to 0.5 (400 to 500 mAU).

TABLE 1

Dyes and $\lambda_{test}$ values for test solutions A-D.

| Test solution | Dye | $\lambda_{test}$ (nm) |
|---|---|---|
| A | MPTS | 404 |
| B | Pyrromethene 556 | 489 |
| C | Sulfarhodamine 101 | 581 |
| D | Cardiogreen | 789 |

Figure 3:
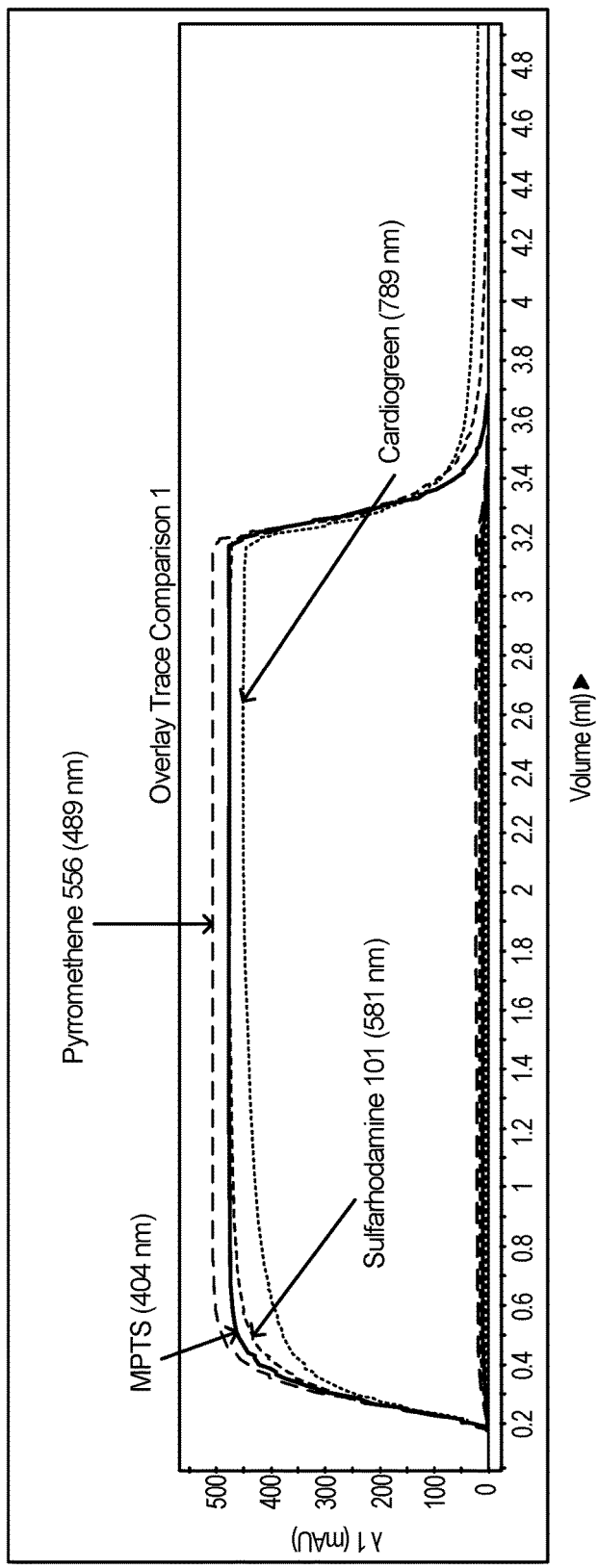
FIG. 3 shows four overlain plots of optical absorbance versus the volume of fluid passing into the output stream of a fluid delivery system. Each plot corresponds to one calibration run of the fluid delivery system in which absorbances at four wavelengths (404, 489, 581, and 789 nm) were measured. As described in Example 2, one test solution containing a dye was injected into the fluid delivery system in each calibration run.

Four calibration runs of a fluid delivery system were performed. In each run, one test solution was injected into an input stream and the other three test solutions were not injected. The output absorbance of the injected test solution was measured continuously, starting at the time of injection, as was the absorbance of the output stream at the $\lambda_{test}$ values for the other three test solutions (FIG. 3).

In each run, the output absorbance of the injected test solution stabilized to approximately 0.4 to 0.5 after a ~1 mL equilibration volume. This output absorbance was not significantly less than the input absorbance, indicating that the injected test solution was not mixed with other test solutions or otherwise diluted. After the same equilibration period, the absorbance of the output stream at the three other $\lambda_{test}$ values was less than 0.025 (25 mAU), reflecting the lack of overlap between the absorbance spectra of the four dyes.

Example 3

Four test solutions were prepared, each containing one dye. The dyes and respective $\lambda_{test}$ values are provided in Table 1. Each test solution was prepared such that the input absorbance of the dye was 0.4 to 0.5 (400 to 500 mAU).

Figure 4:
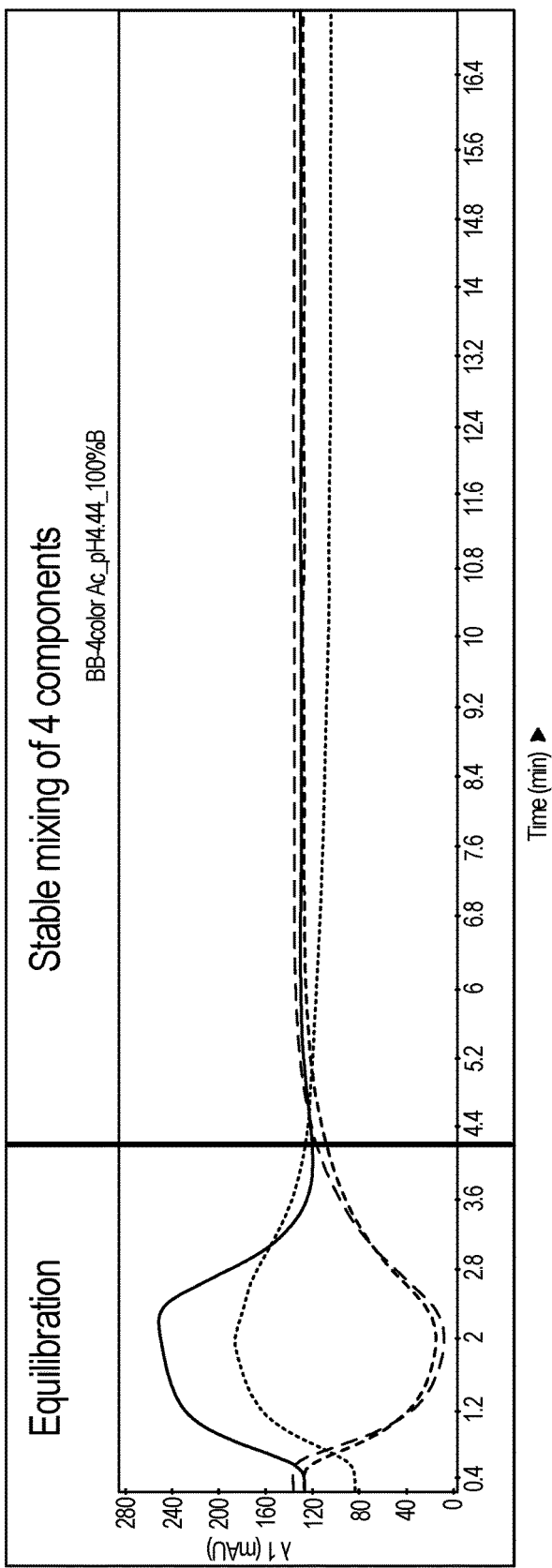
FIG. 4 is a plot of optical absorbance, measured at four wavelengths (404, 489, 581, and 789 nm), versus time. The plot corresponds to one calibration run of a fluid delivery system in which four test solutions were injected. As described in Example 3, each test solution contained a different dye, and the target portion for each test solution in the output stream was 0.25.

One run of a fluid delivery system was performed, in which each test solution was injected into one of the input streams. The test solutions were mixed according to a 0.25 target portion for each test solution. The output absorbances of all four test solutions were measured continuously, starting at the time of injection (FIG. 4). After a ~4 minute equilibration time, the output absorbances of each test solution stabilized to ~0.100 to 0.125 (100 to 125 mAU), or approximately one-quarter the value of the input absorbance. For each test solution, the ratio of the output absorbance to the input absorbance was roughly equal to the target portion, indicating that the fluid delivery system was well calibrated.

Example 4

Four test solutions were prepared, each containing one dye. The dyes and respective $\lambda_{test}$ values are provided in Table 1. Each test solution was prepared such that the input absorbance of the dye was 0.4 to 0.5 (400 to 500 mAU).

One run of a fluid delivery system was performed, in which each test solution was injected into one of the input streams. The test solutions were mixed according to the target portions indicated in Table 2.

TABLE 2

Target portions of test solutions A-D in Example 4.

| Test solution | Dye | Target portion |
|---|---|---|
| A | MPTS | 0.025 |
| B | Pyrromethene 556 | 0.475 |
| C | Sulfarhodamine 101 | 0.500 |
| D | Cardiogreen | 0 |

Figure 5:
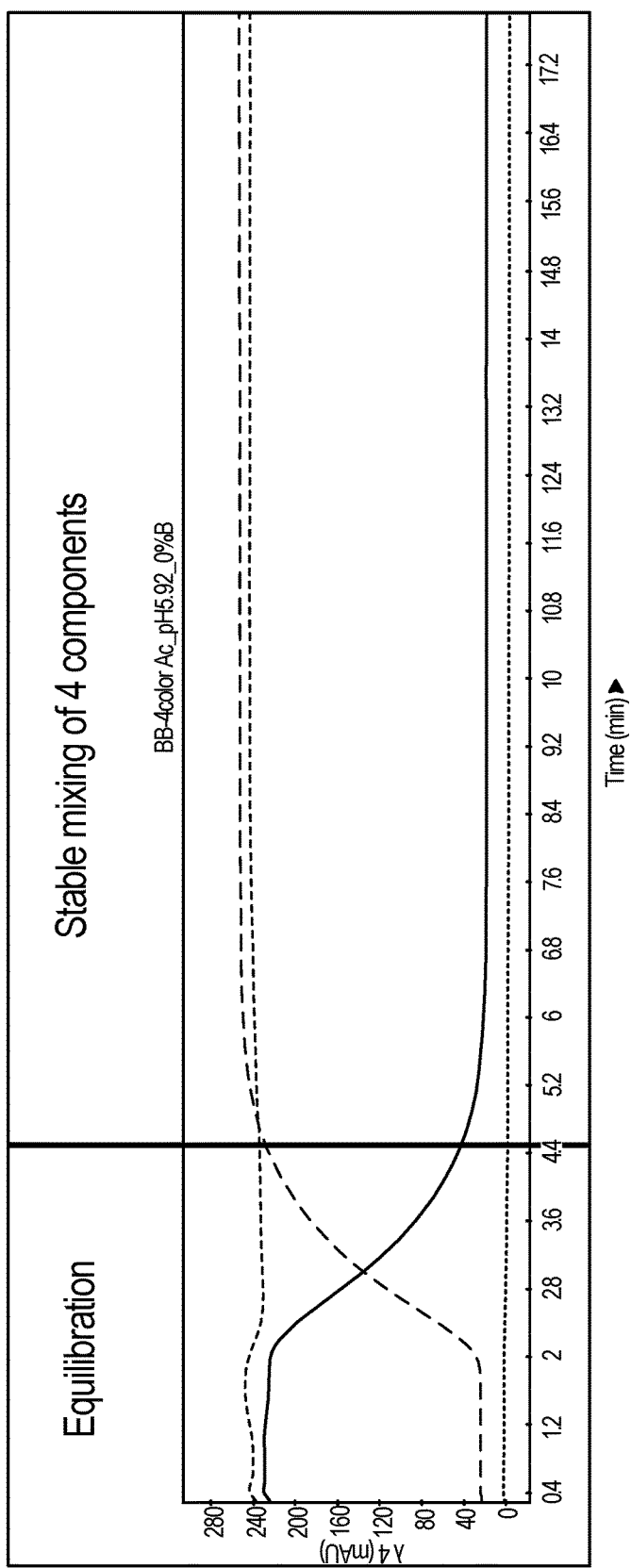
FIG. 5 is a plot of optical absorbance, measured at four wavelengths (404, 489, 581, and 789 nm), versus time. The plot corresponds to one calibration run of a fluid delivery system in which four test solutions were injected. As described in Example 4, each test solution contained a different dye. The target portions for the test solutions in the output stream varied from 0 to 0.5.

The output absorbances of all four test solutions were measured continuously, starting at the time of injection (FIG. 5). After a ~4 minute equilibration time, the output absorbances of test solutions B and C stabilized to approximately 0.240 (240 mAU). The output absorbance of test solution A stabilized to approximately 0.020 (20 mAU) and the output absorbance of test solution D did not rise above baseline. For each test solution, the ratio of the output absorbance to the input absorbance was roughly equal to the target portion, indicating that the fluid delivery system was well calibrated.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of calibrating a fluid delivery system, the method comprising:
   providing a fluid delivery system connected to N input streams, wherein N is an integer greater than or equal to two, and wherein the fluid delivery system mixes together fluids from the N input streams to form an output stream;
   obtaining N test solutions, wherein each test solution comprises a dye having a characteristic wavelength of maximum absorbance ($\lambda_{max}$);
   for each of the N test solutions,
      designating a wavelength $\lambda_{test}$, wherein $\lambda_{test}$ is within the range from 90% of $\lambda_{max}$ to 110% of $\lambda_{max}$, and
      providing an input absorbance of the test solution, the input absorbance being the absorbance of the solution at $\lambda_{test}$;
   injecting the N test solutions into the N input streams;
   mixing the N test solutions in the fluid delivery system;
   measuring the absorbance of the output stream at N wavelengths, the wavelengths being the $\lambda_{test}$s designated for the test solutions, thereby obtaining an output absorbance for each test solution; and
   comparing the input absorbance with the output absorbance for each test solution, thereby calibrating the fluid delivery system.

2. A method of iteratively calibrating a fluid delivery system, the method comprising:
   providing a fluid delivery system connected to N input streams, wherein N is an integer greater than or equal to two and wherein the fluid delivery system mixes together fluids from the N input streams to form an output stream;
   providing N test solutions;
   designating a target portion for at least one test solution in the output stream;
   calibrating the fluid delivery system a first time according to claim 1;
   adjusting operation of the fluid delivery system based upon the input absorbance and the output absorbance of the at least one test solution, and the target portion of the at least one test solution in the output stream;
   calibrating the fluid delivery system a second time according to claim 1; and
   further adjusting operation of the fluid delivery system based upon the change in the output absorbance of the at least one test solution between calibrating the fluid delivery system the first time and calibrating the fluid delivery system the second time.

3. The method of claim 2, wherein $\lambda_{max}$ of the dye of any first test solution differs from $\lambda_{max}$ of the dye of any second test solution by at least 50, 100, 200, or 300 nm.

4. The method of claim 2, wherein the $\lambda_{test}$ designated for any first test solution differs from the $\lambda_{test}$ designated for any second test solution by at least 50, 100, 200, or 300 nm.

5. The method of claim 2, wherein the absorbance of any first test solution at the $\lambda_{max}$ of the dye of the first test solution is at least 10 times greater than the absorbance of any second test solution at the same $\lambda_{max}$.

6. The method of claim 2, wherein the absorbance of any particular test solution at the $\lambda_{max}$ of the dye of the particular test solution is at least 10 times greater than the sum of the absorbances of the remaining test solutions at the same $\lambda_{max}$.

7. The method of claim 2, wherein the dyes of the test solutions are sulfonated aromatic dyes.

8. The method of claim 7, wherein the dyes of the test solutions are selected from the group consisting of pyrenes, boron-dipyrromethenes (BODIPYs), rhodamines, and indocyanines.

9. The method of claim 7, wherein the dyes of the test solutions are selected from the group consisting of MPTS, pyrromethene 556, sulforhodamine 101, and cardiogreen.

10. The method of claim 2, wherein the fluid delivery system comprises a valve associated with at least two input streams.

11. The method of claim 10, wherein the valve is associated with all N input streams.

12. The method of claim 2, further comprising adjusting the operation of the fluid delivery system based upon the input absorbance and the output absorbance of at least one test solution.

13. The method of claim 2, wherein said comparing comprises, for each test solution, dividing the output absorbance by the input absorbance to obtain a ratio, said ratio providing an estimate of the portion of the output stream comprising the test solution.

14. The method of claim 13, wherein the ratios for the N test solutions are all at least 0.001.

15. The method of claim 13, further comprising:
for each test solution,
designating a target portion for the test solution in the output stream, and
comparing the ratio with the target portion;
and wherein said mixing occurs according to the target portions for the test solutions.

16. The method of claim 15, wherein the target portions for the N test solutions are all at least 0.001.

17. The method of claim 15, further comprising adjusting the operation of the fluid delivery system based upon the ratio and the target portion for at least one of the test solutions.

18. The method of claim 17, wherein said adjusting comprises reducing the difference between the ratio and the target portion for at least one of the test solutions.

* * * * *